(12) United States Patent
Torkildsen

(10) Patent No.: US 6,332,351 B1
(45) Date of Patent: Dec. 25, 2001

(54) DETECTION OF SALT CONTENT OF WATER THROUGH MEASUREMENT OF RADIATION ATTENUATION

(75) Inventor: Bernt Helge Torkildsen, Bergen-Sandviken (NO)

(73) Assignee: Framo Engineering A.S., Sandsli (NO)

( * ) Notice: Subject to any disclaimer, the term of this patent is extended or adjusted under 35 U.S.C. 154(b) by 0 days.

(21) Appl. No.: 09/230,923

(22) PCT Filed: Aug. 1, 1997

(86) PCT No.: PCT/GB97/02082

§ 371 Date: Feb. 3, 1999

§ 102(e) Date: Feb. 3, 1999

(87) PCT Pub. No.: WO98/05947

PCT Pub. Date: Feb. 12, 1998

(30) Foreign Application Priority Data

Aug. 5, 1996 (GB) .................................................. 9616452

(51) Int. Cl.$^7$ .................................................. G01N 23/08

(52) U.S. Cl. .................. 73/61.48; 378/53; 73/61.79; 250/432 R; 250/253; 250/269.3

(58) Field of Search ................................ 73/61.48, 61.79; 378/53, 47; 250/253, 261, 269.2, 269.3, 432 R

(56) References Cited

U.S. PATENT DOCUMENTS

| 4,025,788 | 5/1977 | Arima et al. ........................... 250/253 |
| 4,352,288 | 10/1982 | Paap et al. ............................. 378/47 |
| 4,490,609 | * 12/1984 | Chevalier ............................... 378/89 |
| 4,558,220 | * 12/1985 | Evans ................................. 250/269.3 |
| 5,247,559 | * 9/1993 | Ohtsuchi et al. ....................... 378/53 |

FOREIGN PATENT DOCUMENTS

| 0 236 623 | 9/1987 | (EP) . |
| 2 071 312 | 9/1981 | (GB) . |
| 2083908 | * 3/1982 | (GB) . |
| 2 088 050 | 6/1982 | (GB) . |

OTHER PUBLICATIONS by Y. Jiang et al., "An experimental study of the suitability of using a gamma densitometer for void fraction measurements in gas–liquid flow in a small diameter tube", *Measurement Science and Technology*, vol. 4, No. 4, Apr. 1993, pp. 496–505.

* cited by examiner

*Primary Examiner*—Hezron Williams
*Assistant Examiner*—Michael Cygan
(74) *Attorney, Agent, or Firm*—Young & Thompson

(57) ABSTRACT

A method of calculating the salt content of water in a multiphase flow which comprises irradiating a body of the multiphase flow with radiation of three distinct energy levels; measuring the intensity of the transmitted radiation at each of the energy levels, and using the measurements of transmitted radiation as obtained from calibration and radiation mass attenuation coefficients for hydrocarbons for each of the energy levels, to calculate a unique function for representing the salt content of the water. The three energy levels can as an example be provided by the radioactive isotope Barium 133 and the radiation mass attenuation coefficients for hydrocarbons can be calculated theoretically or derived from static calibration measurements. The invention is particularly suited for the measurement of water salinity in a stream comprising a mixture of oil, water, and gas, i.e., a multiphase flow, without separating the phases. It is required to accurately determine the water phase salinity and to use the measurement to calibrate the other sensors or measuring equipment. In addition, the water salinity is often of interest to the well operators as an absolute value which may then be compared with other wells or monitored over a period of time.

5 Claims, 1 Drawing Sheet

DETECTION OF SALT CONTENT OF WATER THROUGH MEASUREMENT OF RADIATION ATTENUATION

BACKGROUND OF THE INVENTION

1. Field of the Invention

The present invention relates to the detection of water constituents and particularly to the measurement of water salinity especially in a stream comprising a mixture of oil, water and gas.

A flowing fluid mixture of oil, water and gas is a common occurrence in the oil industry being a product of an unprocessed well stream. Such a flow mixture is referred to as a multiphase flow in which the oil, water and gas are considered as different phases. It is often required to know characteristics of individual phases within such a multiphase fluid flow for example the salinity of the water phase, and to measure these characteristics without separating the phases.

The salinity of the water phase can affect the accuracy of sensors and measurement methods applied for multiphase measurements It is required therefore to accurately determine the water phase salinity and to use the measurement to calibrate the other sensors or measuring equipment. Alternatively the water salinity is often of interest to the well operators as an absolute value which may then be compared with other wells or monitored over a period of time.

2. Description of the Related Art

Water phase salinity can be calculated according to the method described in EP 0 236 623. This prior art teaches irradiating the multiphase fluid flow with radiation at four distinct energy levels and taking measurements of the incident and transmitted radiation to do calculations involving at least radiation measurements of the four distinct energy levels. This known method requires at least two different radiation isotopes and has the disadvantage of being very sensitive to errors in the measured oil, water and gas path lengths and densities. It is also expensive to use two isotopes and to all intents and purposes this prior art does not provide a satisfactory method of measuring salinity in the water phase in a practical situation. It is only accurate and suitable for controlled laboratory conditions.

SUMMARY OF THE INVENTION

According to the present invention there is provided a method of calculating the salt content of water in a multiphase flow, the method comprising:

irradiating a body of the multiphase flow with radiation of three distinct energy levels;

measuring the intensity of the transmitted radiation at each of the energy levels;

using the measurements of transmitted radiation together with the incident radiation as obtained from calibration and radiation mass attenuation coefficients for hydrocarbons for each of the energy levels, to calculate a unique function representing the salt content of the water.

The three energy levels can as an example be provided by the radioactive isotope Barium 133.

According to a preferred embodiment the radiation mass attenuation coefficients for hydrocarbons can be calculated theoretically or derived from static calibration measurements.

BRIEF DESCRIPTION OF THE DRAWINGS

The FIGURE is a graph illustrating a relationship between $\Gamma$ and water salinity.

DESCRIPTION OF THE PREFERRED EMBODIMENTS

Figure 1:
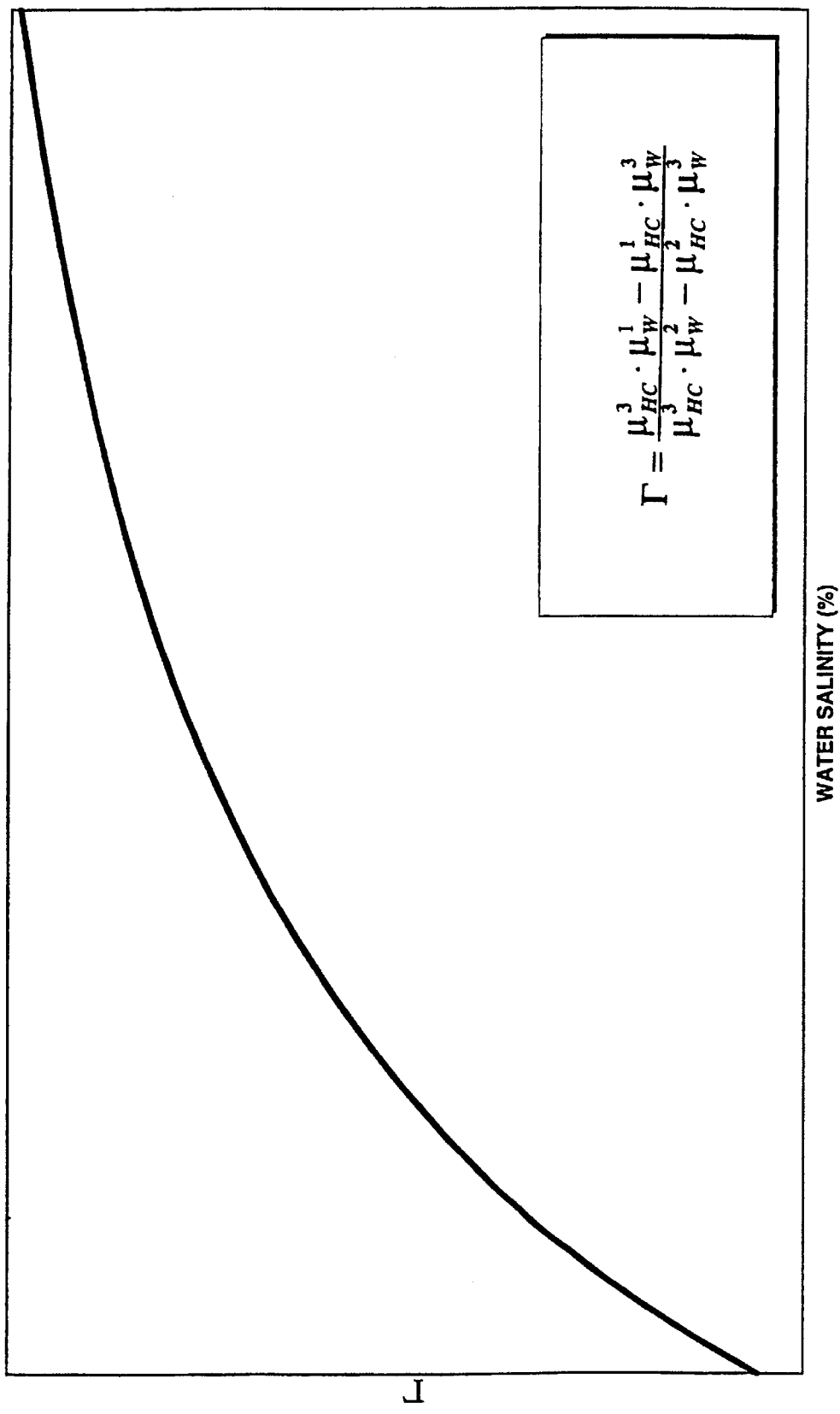

An example will now be described of how the invention ay be carried into effect.

It is well known that radiation impinging on any material is attenuated as it passes through by an amount which is dependent on the intensity of the transmitted radiation, the density of the material, the distance the radiation has travelled and by the type of material, i.e. by its radiation mass attenuation coefficient. This can be expressed in equation form as:

$$N = N_0 \cdot e^{-\rho \mu \chi} \quad \text{Equation (1)}$$

where

N is the intensity of transmitted radiation $N_0$ is the intensity of incidental radiation $\rho$ is the density of the material $\mu$ is the radiation mass attenuation coefficient $\chi$ is the path length in the material.

For a multiphase fluid flow, the different phases must be taken into account and Equation (1) becomes:

$$\frac{\text{Ln}\left(\frac{N_0}{N}\right)}{D} = \sum_{O,W,G} (\rho \cdot \mu \cdot h) \quad \text{Equation (2)}$$

where the subscript "i" indicates a fluid (oil, water or gas) phase, $h_i$ is the phase path length fraction D is the internal pipe diameter or the total path length O, W and G indicates oil, water and gas respectively.

The radiation mass attenuation coefficient ($\mu$) of a material is dependent on the energy level of the impinging radiation, but for a single, particular energy level is a characteristic of the material itself.

For a distinct energy level we can write:

$$\mu_i = \sum_{ELEMENTS} (\mu \cdot \omega)_k \quad \text{Equation (3)}$$

where $\chi$ indicates an element $\omega_\chi$ is the mass fraction of the element $\chi$ $\mu_\chi$ is the mass attenuation coefficient of the element $\chi$ Using superscripts 1, 2 and 3 to denote the three radiation energy levels gives:

$$\frac{\text{Ln}\left(\frac{N_0}{N}\right)^1}{D} = \sum_{O,W,G} (\rho \cdot \mu \cdot h)_i^1 \quad \text{Equation (4)}$$

$$\frac{\text{Ln}\left(\frac{N_0}{N}\right)^2}{D} = \sum_{O,W,G} (\rho \cdot \mu \cdot h)_i^2 \quad \text{Equation (5)}$$

$$\frac{\text{Ln}\left(\frac{N_0}{N}\right)^3}{D} = \sum_{O,W,G} (\rho \cdot \mu \cdot h)_i^3 \qquad \text{Equation (6)}$$

For a given material the radiation mass attenuation coefficient does not change. The coefficient of hydrocarbon oil and gas can therefore be considered equal and constant for a long period. However, for water the coefficient will vary depending upon the salt content. Hence:

$$\mu_O{}^j = \mu_G{}^j = \mu_{HC}{}^j, \ j=1,2,3, \qquad \text{Equation (7)}$$

Applying these to a multiphase fluid flow of hydrocarbons (oil and gas) with water in a closed system such as the uniform pipe, it is evident that the sum of the three phase path length fractions will equal unity and this is known as the closure law and can be represented:

$$\sum_{O,W,G} h_i = 1 \qquad \text{Equation (8)}$$

where $h_i$ is the path length fraction for each of oil (O), water (W) and gas (G).

Combining Equations (4), (5), (6), (7) and (8) it is possible to derive three independent expressions for the water path length fraction $h_w$. Selecting two such expressions based on combinations of energy levels 1 and 3 and energy levels 2 and 3 respectively we can write:

$$h_w^{(1-3)} = \frac{\mu_{HC}^3 \cdot \text{Ln}\left(\frac{N_0}{N}\right)^1 - \mu_{HC}^1 \cdot \text{Ln}\left(\frac{N_0}{N}\right)^3}{\rho_w \cdot D \cdot (\mu_w^1 \cdot \mu_{HC}^3 - \mu_w^3 \cdot \mu_{HC}^1)} \qquad \text{Equation (9)}$$

$$h_w^{(2-3)} = \frac{\mu_{HC}^3 \cdot \text{Ln}\left(\frac{N_0}{N}\right)^2 - \mu_{HC}^2 \cdot \text{Ln}\left(\frac{N_0}{N}\right)^3}{\rho_w \cdot D \cdot (\mu_w^2 \cdot \mu_{HC}^3 - \mu_w^3 \cdot \mu_{HC}^2)} \qquad \text{Equation (10)}$$

These two expressions will have different sensitivity to the water salt content because the level of influence on the radiation mass attenuation depends on the actual radiation energy level. A unique solution for both the water path length fraction and the water salt content can therefore be obtained by equating these two expressions.

Thus:

$$h_w^{(1-3)} = h_w^{(2-3)} \qquad \text{Equation (11)}$$

which gives:

$$h_w^{(1-3)} = \qquad \text{Equation (12)}$$

$$\frac{\mu_{HC}^3 \cdot \text{Ln}\left(\frac{N_0}{N}\right)^1 - \mu_{HC}^1 \cdot \text{Ln}\left(\frac{N_0}{N}\right)^3}{\mu_{HC}^3 \cdot \text{Ln}\left(\frac{N_0}{N}\right)^2 - \mu_{HC}^2 \cdot \text{Ln}\left(\frac{N_0}{N}\right)^3} = \frac{\mu_{HC}^3 \cdot \mu_w^1 - \mu_{HC}^1 \cdot \mu_w^3}{\mu_{HC}^3 \cdot \mu_w^2 - \mu_{HC}^2 \cdot \mu_w^3}$$

The right hand side of this Equation (12) is a unique function of the salt content in the water. The relation can be found theoretically from Equation (3), or obtained from static calibration.

The left hand side of Equation (12) can be calculated based on measurements of the transmitted radiation intensities when the incident radiation intensities and the radiation mass attenuation coefficient for hydrocarbon are known.

This relationship is illustrated in the graph of FIG. 1.

Thus the water salinity can be calculated independent of the path length fractions or the densities of each of the three phases.

The three energy levels of radiation can be derived from a single source such as the radioactive isotope Barium 133. The Barium 133 source provides simultaneous radiation of 32 keV, 80 keV and 356 keV and is ideally suitable. However other isotopes could equally be used, or any combination of isotopes, provided that at least three energy levels of radiation are generated.

The salinity value thus achieved may be printed out or displayed as an absolute value and/or may be used to provide calibration data or fed as a direct signal for auto calibration of sensors and measurement arrangements so as to reduce or eliminate the effect of the water salinity on those sensors and arrangements. Examples include measurements based on attenuation of $\chi$- and $\gamma$-rays, absorption of microwaves, capacitance or inductance, or any other measurements influenced by water salinity.

What is claimed is:

1. A mthod of calculating the salt content of water in a multiphase stream comprising oil, water and gas phases, the method comprising:

irradiating a body of multiphase stream with radiation of at least three distinct energy levels;

measuring the intensity of the transmitted radiation at each of the three energy levels;

using the measurements of transmitted radiation intensity from only three energy levels of the irradiating radiation, together with incident radiation intensity and radiation mass attenuation coefficients for hyddrocarbons for each of the energy levels, to calculate a unique function representing the salt content of the water, phase independently of the proportions and densities of the oil, water and gas phases.

2. A method according to claim 1, wherein the three energy levels are provided by the radioactive isotope Barium 133.

3. A method according to claim 1, wherein the radiation mass attenuation coefficients are obtained by static calibration.

4. A method according to claim 1, comprising displaying the calculated salt content as a value.

5. A method according to claim 1, comprising using the calculated salt content of the water phase to calibrate other sensors and measuring arrangements.

* * * * *